US011427666B2

(12) United States Patent
Liao et al.

(10) Patent No.: US 11,427,666 B2
(45) Date of Patent: Aug. 30, 2022

(54) SILICONE-CONTAINING ACRYLIC POLYMERS FOR TRANSDERMAL DRUG DELIVERY COMPOSITIONS

(71) Applicant: NOVEN PHARMACEUTICALS, INC., Miami, FL (US)

(72) Inventors: Jun Liao, Miami, FL (US); Jilin Zhang, Miami, FL (US); Puchun Liu, Miami, FL (US); Steven Dinh, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

(21) Appl. No.: 16/592,643

(22) Filed: Oct. 3, 2019

(65) Prior Publication Data

US 2020/0277424 A1 Sep. 3, 2020

Related U.S. Application Data

(63) Continuation of application No. 14/810,962, filed on Jul. 28, 2015, now abandoned.

(60) Provisional application No. 62/031,325, filed on Jul. 31, 2014.

(51) Int. Cl.

| C08F 230/08 | (2006.01) |
|---|---|
| A61K 31/4458 | (2006.01) |
| A61K 31/137 | (2006.01) |
| A61K 31/27 | (2006.01) |
| A61K 31/4525 | (2006.01) |
| A61K 31/4168 | (2006.01) |
| A61K 9/70 | (2006.01) |

(52) U.S. Cl.
CPC .......... *C08F 230/08* (2013.01); *A61K 9/7061* (2013.01); *A61K 31/137* (2013.01); *A61K 31/27* (2013.01); *A61K 31/4168* (2013.01); *A61K 31/4458* (2013.01); *A61K 31/4525* (2013.01)

(58) Field of Classification Search
CPC . C08F 230/08; A61K 31/4458; A61K 31/137; A61K 31/27; A61K 31/4525; A61K 31/4168; A61K 9/7061
See application file for complete search history.

(56) References Cited

U.S. PATENT DOCUMENTS

| 5,288,827 | A | * | 2/1994 | Li | ............. | C08F 230/08 |
|---|---|---|---|---|---|---|
| | | | | | | 526/279 |
| 5,474,783 | A | | 12/1995 | Miranda et al. | | |
| 8,124,689 | B2 | * | 2/2012 | Loubert | .................. | A61P 25/18 |
| | | | | | | 525/100 |
| 8,153,151 | B2 | | 4/2012 | Houze | | |
| 8,715,723 | B2 | | 5/2014 | Kanios et al. | | |
| 2005/0169977 | A1 | | 8/2005 | Kanios et al. | | |
| 2006/0078603 | A1 | | 4/2006 | Nguyen | | |
| 2007/0212410 | A1 | | 9/2007 | Kanios et al. | | |
| 2014/0105979 | A1 | | 4/2014 | Liao et al. | | |
| 2014/0121611 | A1 | | 5/2014 | Lambert | | |
| 2014/0188056 | A1 | * | 7/2014 | Mori | ........................ | A61P 29/00 |
| | | | | | | 604/290 |
| 2014/0271865 | A1 | * | 9/2014 | Lambert | ............... | A61K 31/137 |
| | | | | | | 424/487 |
| 2014/0276478 | A1 | | 9/2014 | Liao et al. | | |
| 2014/0276483 | A1 | | 9/2014 | Liao et al. | | |
| 2014/0322298 | A1 | | 10/2014 | Nguyen et al. | | |
| 2015/0104495 | A1 | | 4/2015 | Nguyen et al. | | |
| 2015/0119828 | A1 | | 4/2015 | Lambert | | |
| 2015/0342899 | A1 | * | 12/2015 | Kulakofsky | ........... | A61K 45/06 |
| | | | | | | 514/401 |
| 2016/0030362 | A1 | | 2/2016 | Liao et al. | | |

FOREIGN PATENT DOCUMENTS

| EP | 0 611 783 A1 | 8/1994 |
|---|---|---|
| WO | WO-2007/067866 A2 | 6/2007 |
| WO | WO-2007/100757 A2 | 9/2007 |
| WO | WO-2007/145996 A2 | 12/2007 |
| WO | WO-2010/124187 A2 | 10/2010 |
| WO | WO-2013/072062 A1 | 5/2013 |
| WO | WO-2014/074289 A1 | 5/2014 |
| WO | WO-2014/106009 A1 | 7/2014 |

OTHER PUBLICATIONS

International Search Report dated Oct. 23, 2015 in application No. PCT/US2015/042370.

\* cited by examiner

*Primary Examiner* — Sean M Basquill
(74) *Attorney, Agent, or Firm* — Foley & Lardner LLP

(57) ABSTRACT

Described herein are silicone-containing acrylic polymers useful, for example, in transdermal drug delivery compositions, to methods of making and using them, to transdermal drug delivery compositions comprising them, and to methods of making and using such transdermal drug delivery compositions. The polymers are particular suitable for formulating amine drugs, such as amphetamine, methylphenidate, rivastigmine, paroxetine and clonidine.

13 Claims, 5 Drawing Sheets

SILICONE-CONTAINING ACRYLIC POLYMERS FOR TRANSDERMAL DRUG DELIVERY COMPOSITIONS

CROSS-REFERENCE TO RELATED APPLICATIONS

The present application is a continuation of U.S. application Ser. No. 14/810,962, filed Jul. 28, 2015, which claims priority to U.S. Provisional Application No. 62/031,325, filed Jul. 31, 2014. The entire contents of each of which are hereby incorporated by reference.

FIELD

The present invention relates generally to silicone-containing acrylic polymers useful, for example, in transdermal drug delivery compositions, to methods of making and using them, to transdermal drug delivery compositions comprising them, and to methods of making and using such transdermal drug delivery compositions.

BACKGROUND

Many factors influence the design and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

A major design choice in the preparation of a transdermal drug delivery composition relates to the polymer components of the composition, e.g., the polymers used in the drug-containing carrier layer and/or any non-drug containing polymer layers. Typically, the polymers are pressure-sensitive adhesives, but different pressure-sensitive adhesive polymers have different properties that make them more or less advantageous for use in a given composition. Factors considered when selecting polymers for use in a transdermal drug delivery composition may include, for example, the solubility of the drug(s) to be formulated in the polymer, whether the polymer includes any reactive moieties that may react with any reactive moieties of the drug or other components of the composition, the physical compatibility of the polymer with other components of the composition, the desired physical properties of the composition (e.g., tackiness and wear properties), the desired pharmacokinetic properties of the composition (e.g., the rate and duration of drug delivery), etc.

Two classes of pressure-sensitive adhesives widely used in transdermal drug delivery compositions include acrylic pressure-sensitive adhesives and silicone pressure-sensitive adhesives. Generally speaking, most drugs exhibit a relatively high solubility in acrylic pressure-sensitive adhesives and a relatively low solubility in silicone pressure-sensitive adhesives. Mixtures of acrylic pressure-sensitive adhesives and silicone pressure-sensitive adhesives have been used to balance these properties. For example, while a drug must be solubilized in the carrier composition in order to be delivered transdermally, high solubility can inhibit drug flux out of the composition such that a high concentration of drug may be required in order to achieve satisfactory (e.g., therapeutically effective) drug flux. Formulating a transdermal drug delivery composition with a high concentration of drug also may undermine the desired physical characteristics of the composition, because many drugs have a plasticizing effect. Further, a relatively large amount of drug may remain in the composition after use. On the other hand, the solubility of many drugs in silicone pressure-sensitive adhesives is not sufficient to achieve satisfactory drug loading and drug flux. However, silicone pressure-sensitive adhesives can be used in combination with acrylic pressure-sensitive adhesives to balance some of the properties outlined above.

Compositions comprising blends of silicone pressure-sensitive adhesives and acrylic pressure-sensitive adhesives suffer from other disadvantages, however. For example, many silicone pressure-sensitive adhesives and acrylic pressure-sensitive adhesives are physically incompatible, such that it is difficult to achieve homogenous blends of the polymers, and blends that are formed may exhibit phase separation during further processing or storage. Moreover, silicone pressure-sensitive adhesives that include silanol groups may be reactive with drugs that have a reactive amine moiety, and may be associated with poor physical properties and chemical stability problems, such as, for example, a release liner peel force that increases over time.

Therefore, there remains a need for polymers that are useful in transdermal drug delivery compositions, including polymers that are useful in transdermal drug delivery compositions for amine group-containing drugs.

SUMMARY OF THE INVENTION

In accordance with some embodiments, there are provided compositions for the transdermal delivery of an amine drug in the form of a flexible finite system for topical application, comprising a polymer matrix comprising a drug and a silicone-containing acrylic polymer. In some embodiments, the silicone-containing acrylic polymer is a non-reactive silicone-containing acrylic polymer made from one or more non-reactive acrylic monomers and one or more non-reactive silicone-containing acrylic monomers, wherein the non-reactive monomers and polymer do not react with amine groups of the amine drug. In some embodiments, the silicone-containing acrylic polymer is made from one or more non-reactive acrylic monomers selected from the group consisting of methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, octyl acrylamide, hydroxyethyl acrylate, and vinyl-group containing monomers, such as vinyl acetate and vinyl pyrrolidone, and one or more non-reactive silicone-containing acrylic monomers, wherein the non-reactive monomers do not react with amine groups of the amine drug. In some embodiments, the silicone-containing acrylic polymer is made from one or more of methyl acrylate monomers, methyl methacrylate monomers, 2-ethylhexyl acrylate monomers, butyl acrylate monomers, amide-containing monomers and/or vinyl group-containing monomers, and one or more non-reactive silicone-containing acrylic monomers, wherein the non-reactive monomers do not react with amine groups of the amine drug.

In accordance with any embodiments, the drug may be an amine drug selected from the group consisting of amphetamine, methylphenidate, rivastigmine, rotigotine, fentanyl, paroxetine clonidine, amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, scopolamine, telenzepine, theophylline, tolterodine, trimipramine, trihexyphenidyl, tropatepine, and tropicamide.

In accordance with any embodiments, composition may further comprise a backing and/or a release liner.

In accordance with other embodiments, there are provided methods for the transdermal delivery of an amine drug, comprising topically applying a composition as described herein to the skin or mucosa of a subject in need thereof.

In accordance with other embodiments, there are provided uses of a silicone-containing acrylic polymer in the preparation of a medicament for the transdermal delivery of an amine drug, such as to provide treatment or prevention of any condition for which the amine drug is useful for treating or preventing.

In accordance with other embodiments, there are provided compositions in the form of a flexible finite system for topical application, comprising a polymer matrix comprising a drug and a silicone-containing acrylic polymer, for use in the transdermal delivery of an amine drug, such as for use in treating or preventing any condition for which the amine drug is useful for treating or preventing.

In accordance with other embodiments, there are provided methods of manufacturing a composition for the transdermal delivery of an amine drug in the form of a flexible finite system for topical application, comprising forming a polymer matrix blend by blending an amine drug and a silicone-containing acrylic polymer in a solvent, applying the polymer matrix blend to a support layer, and removing any remaining solvent.

In accordance with other embodiments, there are provided methods of manufacturing a silicone-containing acrylic polymer, comprising copolymerizing acrylic monomers with silicone-containing acrylic monomers. In specific embodiments, the acrylic monomers and silicone-containing acrylic monomers are non-reactive with amine groups. In some embodiments, the silicone-containing acrylic polymer is comprised of 1-99% by weight acrylic monomers and 99-1% by weight silicone-containing acrylic monomers, based on the total dry weight of the polymer. In some embodiments, the silicone-containing acrylic polymer is comprised of up to 50% by weight acrylic monomers and at least 50% by weight silicone-containing acrylic monomers, based on the total dry weight of the polymer. In other embodiments, the silicone-containing acrylic polymer is comprised of at least 50% by weight acrylic monomers and up to 50% by weight silicone-containing acrylic monomers, based on the total dry weight of the polymer.

DETAILED DESCRIPTION

Figure 1:
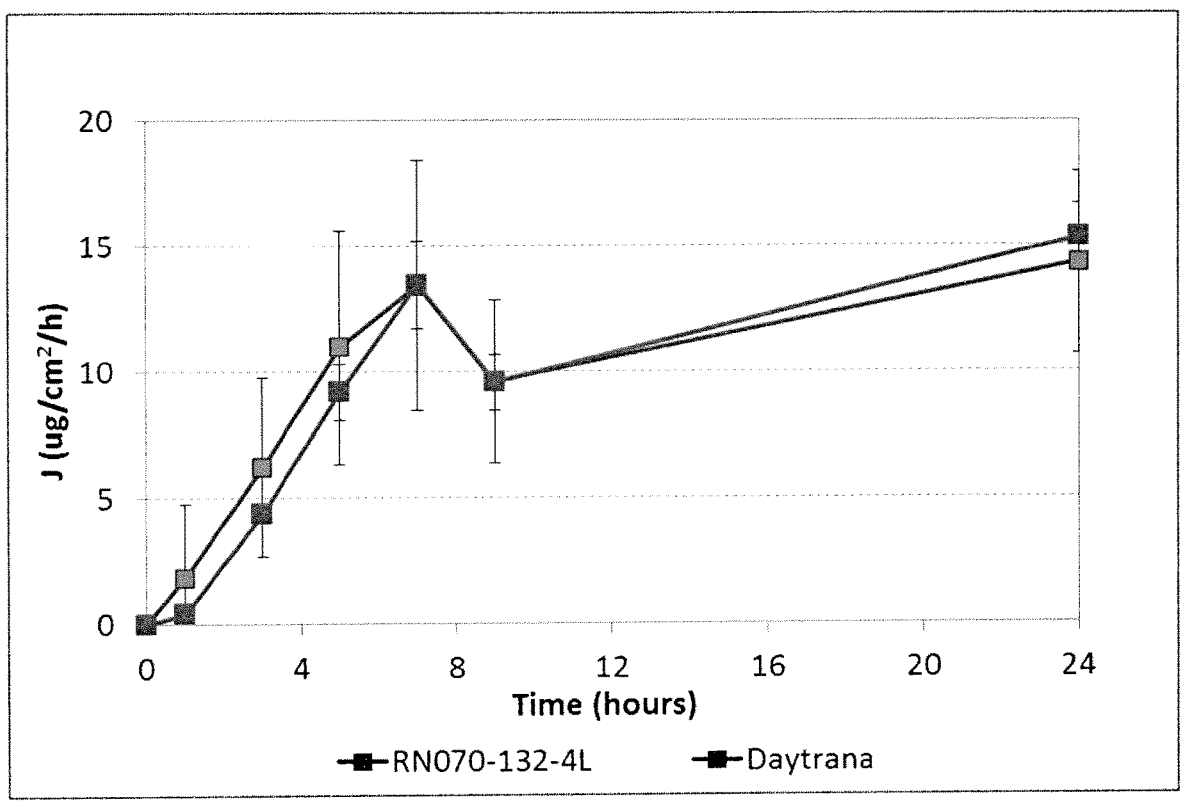
FIG. 1 shows in vitro flux data (flux, $\mu g/cm^2/hr$) of methylphenidate from a composition comprising a silicone-containing acrylic polymer as described herein as compared to Daytrana®.

Described herein are silicone-containing acrylic polymers useful, for example, in transdermal drug delivery compositions. In specific embodiments, the polymers are suitable for use with amine drugs.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

As used herein "subject" denotes any mammal in need of drug therapy, including humans. For example, a subject may be suffering from or at risk of developing a condition that can be treated or prevented with an amine drug, or may be taking an amine drug health maintenance purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of an amine drug.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein, "active surface area" means the surface area of the drug-containing polymer matrix of the transdermal drug delivery system.

The compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches. The compositions comprise a drug-containing polymer matrix that releases an active agent (such as an amine drug) upon application to the skin (or any other surface noted above). In some embodiments, the composition in flexible, finite form may include a backing layer and/or a release liner layer in addition to a drug-containing polymer matrix layer.

As used herein, "drug-containing polymer matrix" refers to a polymer composition which contains one or more drugs, such as an amine drug, and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents, skin permeation enhancers, or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

As used herein, the term "non-reactive component" identifies components that do not contain functional groups with active hydrogen atoms or functional groups with hydrogen atoms available for chemical reaction or interaction with an amine drug, such as, for example, carboxyl, hydroxyl, amine, thiol, silanol, sulfoxyl, or epoxy groups. As used herein, non-reactive components may include amide group-containing monomers (e.g., components with amido groups).

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc.

As used herein, the term "amine drugs" refers to any physiologically active agent comprising an amine group, including a primary, secondary, and/or tertiary amine group. Non-limiting examples of amine drugs include amphetamine, methylphenidate, rivastigmine, rotigotine, fentanyl, paroxetine, and clonidine. Further examples are discussed in more detail below.

Silicone-Containing Acrylic Polymers

Described herein are silicone-containing acrylic polymers that can be made by copolymerizing acrylic monomers with silicone-containing acrylic monomers. In specific embodiments, the monomers do not include functional groups that are reactive with amine drugs, as discussed in more detail below. That is, in specific embodiments, the monomer are non-reactive monomers, as discussed in more detail below. In further specific embodiments, the polymers are comprised only of non-reactive monomers, such that the polymers are non-reactive.

As used herein, "non-reactive monomer" and "non-reactive polymer" includes any monomers or polymers that do not include functional groups that are reactive with amine groups of amine drugs.

As used herein, "functional groups," are reactive chemical groups present on acrylic-based monomer units which modify the acrylic-based polymers directly or which provide sites for further reactions. As used herein, "functional groups," includes chemical groups that are reactive with amine groups of amine drugs, and that are not reactive with amine groups of amine drugs. General examples of functional groups include carboxyl, epoxy, hydroxyl, sulfoxyl, and amino groups. Typical carboxyl functional monomers include acrylic acid, methacrylic acid, itaconic acid, maleic acid, and crotonic acid. Typical hydroxyl functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. Of these functional groups, "non-reactive" functional groups are those groups that are not reactive with amine groups of amine drugs. Thus, for example, hydroxyl groups and amino groups are "non-reactive" functional groups in the context of amine drugs. Vinyl esters, such as vinyl acetate, may be reactive with primary amine drugs (e.g., amphetamine) and secondary amine drugs (e.g., methylphenidate), but are not generally reactive (e.g., are "non-reactive") with tertiary amine drugs, (e.g., rivastigmine and fentanyl). Thus, in some embodiments, polymers with these functional groups can be included in a composition as "non-reactive" polymers, depending on the drug being formulated. As noted above, in some embodiments, the acrylic polymer does not include reactive functional groups, such as carboxyl, epoxy, and sulfoxyl groups, which are generally reactive with amine drugs.

Examples of suitable non-reactive acrylic monomers include alkyl acrylates and alkyl methacrylates, such as methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate, amide-group containing-monomers such as octyl acrylamide. As noted above, depending on the drug being formulated, additional suitable non-reactive acrylic monomers may include, hydroxyl-containing monomers such as hydroxyethyl acrylate, and vinyl group-containing monomers such as vinyl acetate and vinyl pyrrolidone.

In specific embodiments, a silicone-containing acrylic polymer as described herein is made from monomers including methyl acrylate, methyl methacrylate, 2-ethylhexyl acrylate, butyl acrylate, amide-containing monomers and vinyl group-containing monomers. In further specific embodiments a silicone-containing acrylic polymer as described herein is made from up to four types of monomers selected from (1) methyl acrylate or methyl methacrylate monomers; (2) 2-ethylhexyl acrylate or butyl acrylate monomers, (3) amide-containing monomers, and (4) vinyl group-containing monomers. Thus, for example, a silicone-containing acrylic polymer as described herein may be made from the following monomers: (1) methyl acrylate or methyl methacrylate; (2) 2-ethylhexyl acrylate or butyl acrylate, (3) optionally, an amide-containing monomer, and (4) optionally, a vinyl group-containing monomer.

Examples of suitable silicone-containing acrylic monomers include acrylic monomers with a silicone moiety, such as siloxy silanes and polydimethylsiloxanes of different molecular weights, such as 3-acryloxypropyl tri(trimethylsiloxy)silane, 3-methacryloxypropyl tri(trimethylsiloxy)silane, mono-vinyl terminated polydimethylsiloxane, (2-acryloxyethyl)-dimethyl-(trimethylsiloxy)-silane, (2-acryloxyethyl)-monomethyl-bis(trimethylsiloxy)-silane, (2-acryloxyethyl)-tris(trimethylsiloxy)-silane, (2-methacryloxyethyl)-dimethyl-(trimethylsiloxy)-silane, (2-methacryloxyethyl)-monomethyl-bis(trimethylsiloxy)-silane, (2-methacryloxyethyl)-tris(trimethylsiloxy)-silane, (2-acryloxy-1-methylethyl)-dimethyl-(trimethylsiloxy)-silane, (2-acryloxy-1-methylethyl)-monomethyl-bis(trimethylsiloxy)-silane, (2-acryloxy-1-methylethyl)-tris(trimethylsiloxy)-silane, (2-methacryloxy-1-methylethyl)-dimethyl-(trimethylsiloxy)-silane, (2-methacryloxy-1-methylethyl)-monomethyl-bis(trimethylsiloxy)-silane, (2-methacryloxy-1-methylethyl)-tris(trimethylsiloxy)-silane, (2-acryloxypropyl)-dimethyl-(trimethylsiloxy)-silane, (2-acryloxypropyl)-monomethyl-bis(trimethylsiloxy)-silane, (2-acryloxypropyl)-tris(trimethylsiloxy)-silane, (2-methacryloxypropyl)-dimethyl-(trimethylsiloxy)-silane, (2-methacryloxypropyl)-monomethyl-bis(trimethylsiloxy)-silane, (2-methacryloxypropyl)-tris(trimethylsiloxy)-silane, (3-acryloxypropyl)-dimethyl-(trimethylsiloxy)-silane, (3-acryloxypropyl)-monomethyl-bis(trimethylsiloxy)-silane, (3-methacryloxypropyl)-dimethyl-(trimethylsiloxy)-silane, (3-methacryloxypropyl)-monomethyl-bis(trimethylsiloxy)-silane, (2-acryloxybutyl)-dimethyl-(trimethylsiloxy)-silane, (2-acryloxybutyl)-monomethyl-bis(trimethylsiloxy)-silane (2-acryloxybutyl)-tris(trimethylsiloxy)-silane, (2-methacryloxybutyl)-dimethyl-(trimethylsiloxy)-silane, (2-methacryloxybutyl)-monomethyl-bis(trimethylsiloxy)-silane. (2-methacryloxybutyl)-tris(trimethylsiloxy)-silane, (3-acryloxybutyl)-dimethyl-(trimethylsiloxy)-silane, (3-acryloxybutyl)-monomethyl-bis(trimethylsiloxy)-silane, (3-acryloxybutyl)-tris(trimethylsiloxy)-silane, (3-methacryloxybutyl)-dimethyl-(trimethylsiloxy)-silane, (3-methacryloxybutyl)-monomethyl-bis(trimethylsiloxy)-silane, (3-methacryloxybutyl)-tris(trimethylsiloxy)-silane, (4-acryloxybutyl)-dimethyl-(trimethylsiloxy)-silane, (4-acryloxybutyl)-monomethyl-bis(trimethylsiloxy)-silane. (4-acryloxybutyl)-tris(trimethylsiloxy)-silane, (4-methacryloxybutyl)-dimethyl-(trimethylsiloxy)-silane, (4-methacryloxybutyl)-monomethyl-bis(trimethylsiloxy)-silane, (4-methacryloxybutyl)-tris(trimethylsiloxy)-silane, (2-acryloxy-2-methylpropyl)-dimethyl-(trimethylsiloxy)-silane, (2-acryloxy-2-methylpropyl)-monomethyl-bis(trimethylsiloxy)-silane, (2-acryloxy-2-methylpropyl)-tris(trimethylsiloxy)-silane. (2-methacryloxy-2-methyl propyl)-dimethyl-(trimethylsiloxy)-silane, (2-methacryloxy-2-methylpropyl)-monomethyl-bis(trimethylsiloxy)-silane, (2-methacryloxy-2-methylpropyl)-tris(trimethylsiloxy)-silane. (2-acryloxy-1,2-dimethylethyl)-dimethyl-(trimethylsiloxy)-silane. (2-acryloxy-1,2-dimethylethyl)-monomethyl-bis(trimethylsiloxy)-silane, (2-acryloxy-1,2-dimethylethyl)-tris(trimethylsiloxy)-silane, (2-methacryloxy-1,2-dimethylethyl)-dimethyl-(trimethylsiloxy)-silane. (2-methacryloxy-1,2-dimethylethyl)-monomethyl-bis(trimethylsiloxy)-silane, (2-methacryloxy-1,2-dimethylethyl)-tris(trimethylsiloxy)-silane, (2-acryloxy-1,1-dimethylethyl)-dimethyl-(trimethylsiloxy)-silane, (2-acryloxy-1,1-dimethylethyl)-monomethyl-bis(trimethylsiloxy)-silane, (2-acryloxy-1,1-dimethylethyl)-tris(trimethylsiloxy)-silane, (2-methacryloxy-1,1-dimethylethyl)-dimethyl-(trimethylsiloxy)-silane, (2-methacryloxy-1,1-dimethylethyl)-monomethyl-bis(trimethylsiloxy)-silane, (2-methacryloxy-1,1-dimethyl ethyl)-tris(trimethylsiloxy)-silane, (2-acryloxy-2,2-dimethylethyl)-dimethyl-(triethylsiloxy)-silane. (2-acryloxy-2,2-dimethylethyl)-monomethyl-bis(trimethylsiloxy)-silane, (2-acryloxy-2,2-dimethylethyl)-tris(trimethylsiloxy)-silane, (2-methacryloxy-2,2-dimethylethyl)-dimethyl-(trimethylsiloxy)-silane, (2-methacryloxy-2,2-dimethylethyl)-monomethyl-bis(trimethylsiloxy)-silane, (2-methacryloxy-2,2-dimethylethyl)-tris(trimethylsiloxy)-silane, (3-acryloxy-1-methylpropyl)-dimethyl-(trimethylsiloxy)-silane, (3-acryloxy-1-methylpropyl)-monomethyl-bis(trimethylsiloxy)-silane, (3-acryloxy-1-methylpropyl)-tris(trimethylsiloxy)-silane, (3-methacryloxy-1-methylpropyl)-dimethyl-(trimethylsiloxy)-silane, (3-methacryloxy-1-methylpropyl)-monomethyl-bis(trimethylsiloxy)-silane, (3-methacryloxy-1-methylpropyl)-tris(trimethylsiloxy)-silane, (3-acryloxy-2-methylpropyl)-dimethyl-(trimethylsiloxy)-silane, (3-acryloxy-2-methylpropyl)-monomethyl-bis(trimethylsiloxy)-silane, (3-acryloxy-2-methylpropyl)-tris(trimethylsiloxy)-silane, (3-methacryloxy-2-methylpropyl)-dimethyl-(trimethylsiloxy)-silane, (3-methacryloxy-2-methylpropyl)-monomethyl-bis(trimethylsiloxy)-silane, and (3-methacryloxy-2-methylpropyl)-tris(trimethylsiloxy)-silane, etc.

In specific embodiments, a silicone-containing acrylic polymer as described herein includes 3-tris(trimethylsilyloxy)silyl)propyl meth-acrylate (TRIS), mono-vinyl terminated polydimethylsiloxane (PDMS), or a combination thereof.

The adhesion properties of the polymers can be selected and adjusted by selecting and controlling the monomers and monomer ratios. In general, the polymer may be comprised of the acrylic monomers and silicone-containing acrylic monomers in any relative amounts. In some embodiments, the polymer is comprised of 1-99% by weight acrylic monomers and 99-1% by weight silicone-containing acrylic monomers, based on the total dry weight of the polymer. In specific embodiments, the polymer is comprised of up to 50% by weight acrylic monomers and at least 50% by weight silicone-containing acrylic monomers, based on the total dry weight of the polymer. In other specific embodiments, the polymer is comprised of at least 50% by weight acrylic monomers and up to 50% by weight silicone-containing acrylic monomers, based on the total dry weight of the polymer.

Polymer Matrix (Drug-Containing Layer)

The silicone-containing acrylic polymers described herein are useful, for example, as a polymer component of a polymer matrix of a transdermal drug delivery composition.

In some embodiments, the transdermal drug delivery composition is a monolithic system wherein the polymer matrix comprising silicone-containing acrylic polymer(s) and active agent(s) is the only polymeric layer of the system (although the system may additionally comprise a backing and release liner). In other embodiments, the transdermal drug delivery composition is a multi-layer system, wherein the silicone-containing acrylic polymer(s) are present in one or more of a drug-containing layer and a non-drug-containing layer.

In accordance with any of these embodiments, the drug-containing layer may consist of the silicone-containing acrylic polymer(s) and active agent(s), e.g., the drug-containing layer is formulated only with the silicone-containing acrylic polymer(s) and active agent(s). Alternatively, the drug-containing layer may include other components. In some embodiments, the drug-containing layer includes other polymer(s), such as may be effective to improve the physical or pharmacokinetic properties of the compositions, such as drug solubility, drug flux, adhesion, resistance to crystal formation, resistance to cold flow, etc. The other polymer(s) may be selected from acrylic polymers, silicone polymers, rubber-based polymers, such as one or more rubber-based pressure-sensitive adhesives, such as natural or synthetic polyisoprene, polybutylene, polyisobutylene, styrene-butadiene polymers, styrene-isoprene-styrene block copolymers (such as Kraton® D1111 KT), hydrocarbon polymers, such as butyl rubber, halogen-containing polymers, such as polyacrylic-nitrile, polytetrafluoroethylene, polyvinylchloride, polyvinylidene chloride, and polychlorodiene, and other copolymers thereof. Additionally or alternatively, as discussed above, the polymer matrix may comprise a non-adhesive polymer, such as ethyl cellulose.

In some embodiments, the drug-containing layer includes one or more other components, including other components typically used in transdermal drug delivery compositions, such as antioxidants, skin permeation enhancers, tackifiers, plasticizers, crosslinking agents, or other excipients known in the art. In some embodiments, any such components are non-reactive, as discussed above.

When silicone-containing acrylic polymers as described herein are used to formulate amine drugs, a higher drug flux can be achieved as compared to formulating the same amount of the same drug in a corresponding composition based on acrylic polymers. Moreover, compositions made using silicone-containing acrylic polymers exhibit good stability and satisfactory (e.g., stable) release liner peel force over time.

Antioxidants

In some embodiments, the polymer matrix includes an antioxidant. In some embodiments, the antioxidant is butylhydroxytoluene (BHT) and/or butylhydroxyanisole (BHA). In other embodiments, the antioxidant is, additionally or alternatively, tertiary-butylhydroquinone (TBHQ), alpha tocopherol, ascorbic-acid, ascorbyl palmitate, propyl gallate, fumaric acid, malic acid, sodium ascorbate, sodium metabisulfite, and the like. In some embodiments, the antioxidant is a non-reactive component as discussed above. In specific embodiments, the antioxidant (or combinations thereof) are used in a total amount of from about 0 to about 1.0% by weight, including from about 0.1 to about 1.0% by weight, such as about 0.1% by weight, about 0.25% by weight, and about 0.5% by weight, based on the dry weight of the polymer matrix.

Penetration Enhancers

In some embodiments, the polymer matrix comprises one or more penetration enhancer(s). A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer. In some embodiments, the penetration enhancer is a non-reactive component as discussed above.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In some embodiments, the polymer matrix does not comprise a penetration enhancer.

When present, a penetration enhancer typically is used in an amount up to about 30% by dry weight of the polymer matrix, including up to 30% by weight, up to about 20% by weight, including 20% by weight, or up to about 10% by weight, up to 10% by weight, or up to 5% by weight, including up to 5% by weight, based on the dry weight of the polymer matrix.

Tackifying Agents

In some embodiments, the polymer matrix comprises one or more tackifying agents, such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. In some embodiments, the polymer matrix includes one or more tackifying agents selected from rosin esters, aliphatic hydrocarbon resins, aromatic hydrocarbon resins, terpene resins, polybutene, and hydrogenated polybutene.

Other Excipients

In some embodiments, the polymer matrix includes one or more thickeners, fillers, and/or other additives or components known for use in transdermal drug delivery systems.

For example, in some embodiments, the polymer matrix includes one or more of soluble and insoluble polyvinylpyrrolidones (PVP), ethylene-vinyl acetate copolymers, cellulose derivatives, and silicone dioxide ($SiO_2$), and other components.

In some embodiments, the polymer matrix includes one or more binders, such as lecithin, which "bind" the other ingredients; one or more rheological agents (thickeners) containing silicone, such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, such as for enhancing the uniform consistency or continuous phase of the composition or coating.

Other additives and excipients include diluents, stabilizers, fillers, clays, buffering agents, biocides, humectants, anti-irritants, preservatives, plasticizing agents, cross-linking agents, flavoring agents, colorants, pigments and the like.

These substances can be present in any amount sufficient to impart the desired properties to the composition, and are typically used in amounts totaling up to 50%, including from about 0.1% to about 30%, by weight based on the dry weight of the polymer matrix. As noted above, in some embodiments, any such components are non-reactive components.

In some embodiments, a drug-containing polymer matrix layer of a transdermal drug delivery composition comprises the following components by weight, based on the dry weight of the drug-containing polymer matrix layer: 1% to 50% drug, including 2% to 30% drug; 50% to 90% silicone-containing acrylic copolymer(s), including 70% to 90% silicone-containing acrylic copolymers; 0% to 50% of other optional components, such as, for example, non-reactive acrylic pressure-sensitive adhesives, tackifiers, antioxidant, absorption enhancers, etc.

Active Agents

As noted above, the silicone-containing acrylic polymers described herein are useful, for example, as a polymer component of a polymer matrix of a transdermal drug delivery composition. In general, the polymers are useful in compositions for the transdermal delivery of any active agent. In specific embodiments, the polymers are used in compositions for the transdermal delivery of amine drugs. When the polymers are used to formulate amine drugs, it can be particularly advantageous to use non-reactive monomers, non-reactive polymers, and other non-reactive components, as discussed above.

As noted above, the term "amine drugs" refers to any physiologically active agent comprising an amine group, including a primary, secondary, and/or tertiary amine group. Non-limiting examples of amine drugs include amphetamine, methylphenidate, rivastigmine, rotigotine, fentanyl, paroxetine and clonidine.

Amphetamine (alpha-methylphenethylamine) is a chiral drug. The commercially available oral amphetamine product Adderall® includes several different amphetamine salts, including amphetamine sulfate, amphetamine saccharate, and amphetamine aspartate monohydrate, in an overall ratio of d-amphetamine to 1-amphetamine of 3:1. Amphetamine may be used, for example, for achieving central nervous system stimulation, for the treatment of Attention Deficit Disorder (ADD) and/or Attention Deficit/Hyperactivity Disorder (ADHD), and/or for the treatment of narcolepsy.

Methylphenidate (a-phenyl-2-piperidineacetic acid methyl ester) is a chiral drug. While commercially available methylphenidate products (such as the oral product Ritalin® tablets and the transdermal product Daytrana® patch) include a 50:50 (racemic) mixture of d- and l-threo-methylphenidate, it is believed that the d-threo-methylphenidate isomer has greater pharmacological activity. The compositions described herein may be formulated with any isomer of methylphenidate, although compositions comprising a racemic mixture of d- and l-threo-methylphenidate, or comprising primarily the d-threo-methylphenidate isomer may be most commercially relevant.

Methylphenidate, including methylphenidate base in particular, has a secondary amine moiety and a methyl ester moiety, and is unstable and undergoes degradation in the presence of reactive functional groups, such as active hydrogen atoms or functional groups with hydrogen atoms available for chemical reaction or interaction with methylphenidate, such as, for example, carboxyl, hydroxyl, amine, thiol, silanol or epoxy groups, which may be present in polymers, enhancers, excipients and other components that typically may be used in transdermal compositions. Major degradants of methylphenidate include ritalinic acid and erythol isomer, whose concentrations increase significantly with increasing amounts (by weight) of functional groups. Such degradation can greatly reduce the amount of the active species present in a composition after storage, thus reducing the amount of active methylphenidate available for drug delivery. Thus, in some embodiments, the methylphenidate compositions described herein are formulated without components that have such functional groups. That is, in some embodiments, the compositions described herein are formulated only with non-reactive components as defined above and discussed in more detail below.

Rivastigmine, (S)-3-[1-(dimethylamino)ethyl]phenyl N-ethyl-N-methylcarbamate, is a tertiary amine drug. It is a parasympathomimetic or cholinergic agent approved for the treatment of mild to moderate dementia of the Alzheimer's type and dementia due to Parkinson's disease. The drug can be administered orally or transdermally. The commercially available transdermal rivastigmine product (Exelon®) is designed for daily use and comprises four layers: a backing layer, a polymer-drug matrix layer, and adhesive layer and a release liner. The Exelon® patch is available in two sizes, a 5 $cm^2$ patch that includes 9 mg rivastigmine and delivers about 4.6 mg rivastigmine in 24 hours, and a 10 $cm^2$ patch that includes 18 mg rivastigmine and delivers about 9.5 mg in 24 hours rivastigmine. (The 10 $cm^2$ patch that provides a dose of 9.5 mg/24 hours is the recommended effective dose.)

Rotigotine, (S)-6-[propyl(2-thiophen-2-ylethyl)amino]-5, 6,7,8-tetrahydronaphthalen-1-ol, is a tertiary amine drug used to treat Parkinson's disease (PD) and restless legs syndrome (RLS). Current 1-day patch products deliver 1, 2, 3, 4, 6 and 8 mg/day of rotigotine for the treatment of Parkinson's disease or restless legs syndrome.

Fentanyl, N-(1-(2-phenylethyl)-4-piperidinyl)-N-phenylpropanamide, a tertiary amine drug is used to treat pain. Current 3-day patch products deliver 12.5, 25, 50, 75 and 100 μg/hr of fentanyl for pain management.

Paroxetine, (3S,4R)-3-[(2H-1,3-benzodioxol-5-yloxy) methyl]-4-(4-fluorophenyl) piperidine, has a secondary amine moiety, and is used to treat major depression, obsessive-compulsive disorder, panic disorder, social anxiety, post-traumatic stress disorder, generalized anxiety disorder and vasomotor symptoms (e.g. hot flashes and night sweats) associated with menopause.

Clonidine, N-(2,6-dichlorophenyl)-4,5-dihydro-1H-imidazol-2-amine, is used to treat high blood pressure, attention-deficit/hyperactivity disorder, anxiety disorders, withdrawal (from either alcohol, opioids or smoking), migraine, menopausal flushing, diarrhea and certain pain conditions. The commercially available transdermal clonidine product, e.g., Catapres-TTS®, is designed to providing continuous systemic delivery of clonidine for 7 days at an approximately constant rate. Catapres-TTS® is available in three sizes, a 3.5 cm$^2$ patch that includes 2.5 mg clonidine and delivers about 0.1 mg clonidine per day, a 7.0 cm$^2$ patch that includes 5 mg clonidine and delivers about 0.2 mg clonidine per day, and a 10.5 cm$^2$ patch that includes 7.5 mg clonidine and delivers about 0.3 mg clonidine per day.

Other tertiary amine drugs include amiodarone, amitriptyline, atropine, benztropine, biperiden, bornaprine, bupivacaine, chlorpheniramine, cinnarizine, clomipramine, cyclopentolate, darifenacin, dexetimide, dicyclomine, diltiazem, diphenhydramine, doxepin, ethopropazine, flavoxate, homatropine, imipramine, loxapine, mazaticol, metixene, oxybutin, oxyphencyclimine, phenglutarimide, physostigmine, piperidolate, pirenzepine, procyclidine, profenamine, propiverine, scopolamine, telenzepine, theophylline, tolterodine, trimipramine, trihexyphenidyl, tropatepine, and tropicamide.

The amount of drug to be incorporated in the polymer matrix varies depending on the specific drug, the desired therapeutic effect, and the length of time for which the system is to provide therapy. Thus, in one embodiment, the composition comprises an amount of drug sufficient to deliver therapeutically effective amounts of drug over the intended application period, such as 12 hours, 24 hours, from 1 day to 3 days, 7 days, or longer, including for 1 day, for 2 days, for 3 days, for 4 days, for 5 days, for 6 days, for 7 days, or for longer.

Backing

Any of the compositions described herein may include a drug impermeable backing or film, adjacent one face of the polymer matrix. (By "impermeable" to the drug is meant that no substantial amount of drug loss through the backing layer is observed.) When present, the backing protects the polymer matrix from the environment and prevents loss of the drug and/or release of other components to the environment during use. Materials suitable for use as backings are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. Suitable backing materials include commercially available backings films, such as breathable backings such as 3M CoTran™ backings which feature low moisture vapor transmission rate and high oxygen transmission, non-breathable laminate backings such as 3M Scotchpak® backings (3M, St. Paul, Minn.) and Dow® backings (Dow Chemical Company, Midland, Mich.).

Release Liner

Any of the compositions described herein may include a release liner, typically located adjacent the opposite face of the system as compared to the backing layer. When present, the release liner is removed from the system prior to use to expose the polymer matrix layer prior to topical application. Materials suitable for use as release liners are well-known known in the art and commercially available, and include silicone-coated polyethylene, polypropylene, polyester, and polystyrene release liners sold under the PRIMELINER™ brand as supplied by Loparex LLC (Cary, N.C.) 3M Scotchpak™ fluoropolymer-coated polyester release liners supplied by 3M (St. Paul, Minn.), such as Scotchpak™ 1020, 1022, 9741, 9742, 9744, 9748 and 9755 (fluoropolymer coated polyester films), and commercially available products of Dow Corning Corporation designated Bio-Release® liner and Syl-off) 7610 (both silicone-based). In some embodiments, when the polymer matrix comprises a silicone-containing acrylic polymer as described herein, a non-silicone containing face adhesive is provided between the polymer matrix and a silicone-coated release liner.

Packaging

The transdermal drug delivery system may be packaged or provided in a package, such as a pouchstock material used in the prior art for transdermal drug delivery systems in general or for transdermal drug delivery systems for the specific tertiary amine drug being formulated (e.g., rivastigmine, fentanyl or rotigotine). For example, DuPont's Surlyn® or Graphic Packaging's Barex® packaging films can be used in a pouchstock material.

Manufacturing Methods

The compositions described here can be prepared by methods known in the art, such as blending (mixing) the polymer(s) and any other components with an appropriate amount of the active agent (drug) in the presence of an appropriate solvent, such as a volatile organic solvent, casting the wet blend onto a release liner, followed by evaporation of the volatile solvent(s) at appropriate drying conditions, laminating the dried drug-in-adhesive layer on the release liner onto a backing film.

An exemplary general method for preparing a unit final product of a composition as described herein in a flexible, finite form, is as follows:

1. Appropriate amounts of one or more polymers, solvent(s) and/or co-solvent(s), and optional other components) are combined and thoroughly mixed together in a vessel.

2. The drug is added to the mixture and agitation is carried out until the drug is uniformly mixed therein.

3. The composition is transferred to a coating operation where it is coated onto a release liner at a controlled specified thickness. The coated composition is then passed through an oven in order to drive off all volatile processing solvents.

4. The composition coated on the release liner is then brought into contact with a backing layer and wound into rolls.

5. Appropriate size and shape delivery systems are die-cut from the roll material and then pouched.

The order of steps, the amount of the ingredients, and the amount and time of agitation or mixing may be important process variables which will depend on the specific polymers, active agents, solvents and/or co-solvents, and optional components used in the composition, but these factors can be adjusted by those skilled in the art. The order in which each method step is performed can be changed if needed without detracting from the invention.

In accordance with any of the embodiments of compositions described herein, the size of the final product is, in some embodiments, in the range of from about 2 cm$^2$ to about 60 cm$^2$, including from about 15 cm$^2$ to about 30 cm$^2$, including 12.5 cm$^2$, 14.5 cm$^2$, 15 cm$^2$, 18.75 cm$^2$, 22.5 cm$^2$, 25 cm$^2$, 30 cm$^2$, 37.5 cm$^2$, and 45 cm$^2$.

Methods of Use

The compositions described herein are useful in methods for the transdermal delivery of active agents, such as amine drugs, including in therapeutic methods for treating conditions for which the active agents are known to be useful, as discussed above. In such embodiments, a composition comprising a therapeutically effective amount of active agent as described herein is topically applied to a subject in need thereof.

In some embodiments, the compositions achieve transdermal delivery of active agent over a period of time of at least about 8 hours, including a period of time of at least about 8 hours to at least about 12 hours, or longer, including up to and including about 24 hours. In some embodiments, the compositions are formulated for daily application.

In other embodiments, the compositions achieve transdermal delivery of active agent over a period of time of at least about 1 day, at least about 2 days, at least about 3 days, at least about 7 days, or longer. In some embodiments, the compositions are formulated for once or twice weekly application.

The compositions described herein achieve a transdermal flux of active agent that is sufficient to have a therapeutic effect. As used herein, "flux" (also called "permeation rate") is defined as the absorption of a drug through skin or mucosal tissue, and is described by Fick's first law of diffusion:

$$J=-D(dCm/dx)$$

where J is the flux in μg or mg/cm²/hr, D is the diffusion coefficient of the drug through the skin or mucosa in cm²/hr and dCm/dx is the concentration gradient of the drug across the skin or mucosa.

In accordance with other embodiments, there are provided compositions as described herein for use in the transdermal delivery of active agent, such as for use by topically application to the skin or mucosa of a subject in need thereof.

The following specific examples are included as illustrative of the compositions described herein. These examples are in no way intended to limit the scope of the invention. Other aspects of the invention will be apparent to those skilled in the art to which the invention pertains.

Example 1

Silicone-containing acrylic copolymers are synthesized by copolymerization using methodologies known in the art. For example, acrylic monomers are copolymerized with silicone-containing acrylic monomers in an appropriate solvent, such as ethyl acetate, with an appropriate initiator, such as 2,2'-azobisisobutyronitrile (AIBN), at an appropriate temperature.

Silicone-containing acrylic copolymer A is prepared as follows: An initial charge containing 9.7 g methyl acrylate (MA), 20.9 g 2-ethylhexyl acrylate (2-EHA), 95.1 g 3-(tris(trimethylsilyloxy)silyl)propyl methacrylate (TRIS), 0.074 g AIBN, and 125.5 g ethyl acetate (solvent) is mixed in a 2-L round bottom flask, which is installed with a thermometer, condenser, stainless steel stirrer, water bath and dropping funnel. Under stirring, the initial charge is heated to 80° C. and allowed to reflux for 15 minutes. Then a mixture of 29.0 g MA, 62.5 g 2-EHA, 285.3 g TRIS, 0.22 g AIBN and 377.0 g ethyl acetate is uniformly added over 2 hours. After the addition, the flask is held at 80° C. to reflux overnight. Then resulting solution containing polymer A is cooled and poured into a container. The solids content of the polymer A solution was tested at 55.8% (w/w).

A similar process was followed to make silicone-containing polymers B, C, D and E. The properties of these polymers are summarized in the following table. The molecular weight of the polymers was measured by the Gel Permeation Chromatography (GPC) method. The adhesive properties were tested according to standard testing procedures.

| | Components (weight ratio) | Avg MW | Probe Tack (g/0.5 cm²) | Release Liner Peel (g/0.5") | Stainless Steel peel (g/0.5") | Shear (min, 0.75" width, 250 g) |
|---|---|---|---|---|---|---|
| A | MA/EHA/TRIS (7.7/16.5/75.8) | 184,926 | 1072 | 11.2 | 1603.7 | 3.7 |
| B | MA/EHA/PDMS (33.3/33.3/33.3) | 460,256 | 14.5 | 0.5 | 86.6 | 78.8 |
| C | MA/EHA/TRIS (20/5/75) | 324,339 | 460.7 | 4.3 | 455.3 | 246.0 |
| D | MA/EHA/TRIS/PDMS (40/10/30/20) | 629,506 | 317.6 | 4.0 | 393.7 | 1414 |
| E | MMA/EHA/TRIS (12.5/7.5/80) | 175,287 | 255 | 15.3 | 333.4 | 201.3 |

PDMS: mono-vinyl terminated polydimethylsiloxane
MMA: methyl methacrylate

As seen from a comparison of the monomer components and polymer properties, the properties of the polymers can be selected, adjusted and controlled by selecting the monomers and monomer ratios. Further, as discussed above, for drugs that are less soluble in silicone polymers than acrylic polymers (e.g. most drugs), increasing the relative amount of the silicone-containing monomer(s) in the polymers is expected to decrease drug solubility, resulting in an increase in drug flux for a given concentration of drug.

Example 2

Methylphenidate was formulated in silicone-containing acrylic polymer B (described above) to prepare a composition comprising 20% methylphenidate and 80% polymer B. Drug flux through human cadaver skin over 24 hours was assessed in vitro. Results as compared to results achieved with the polymer matrix of the commercial Daytrana® product (20% methylphenidate, 80% blend of acrylic pressure-sensitive adhesive polymer and silicone pressure-sensitive adhesive polymer) are shown in FIG. 1 and summarized below.

| Lot # | Formulation (SP 9732 Backing) | 94 hr Flux (mcg/cm²/h) | Flux Ratio |
|---|---|---|---|
| 65654 | Daytrana | 9.10 | 1.0 |
| RN070-132-4L | 20% MPH + 80% Copolymer B | 10.48 | 1.15 |

The results show that the composition based on polymer B achieved a drug flux comparable to that of Daytrana®.

Figure 2:
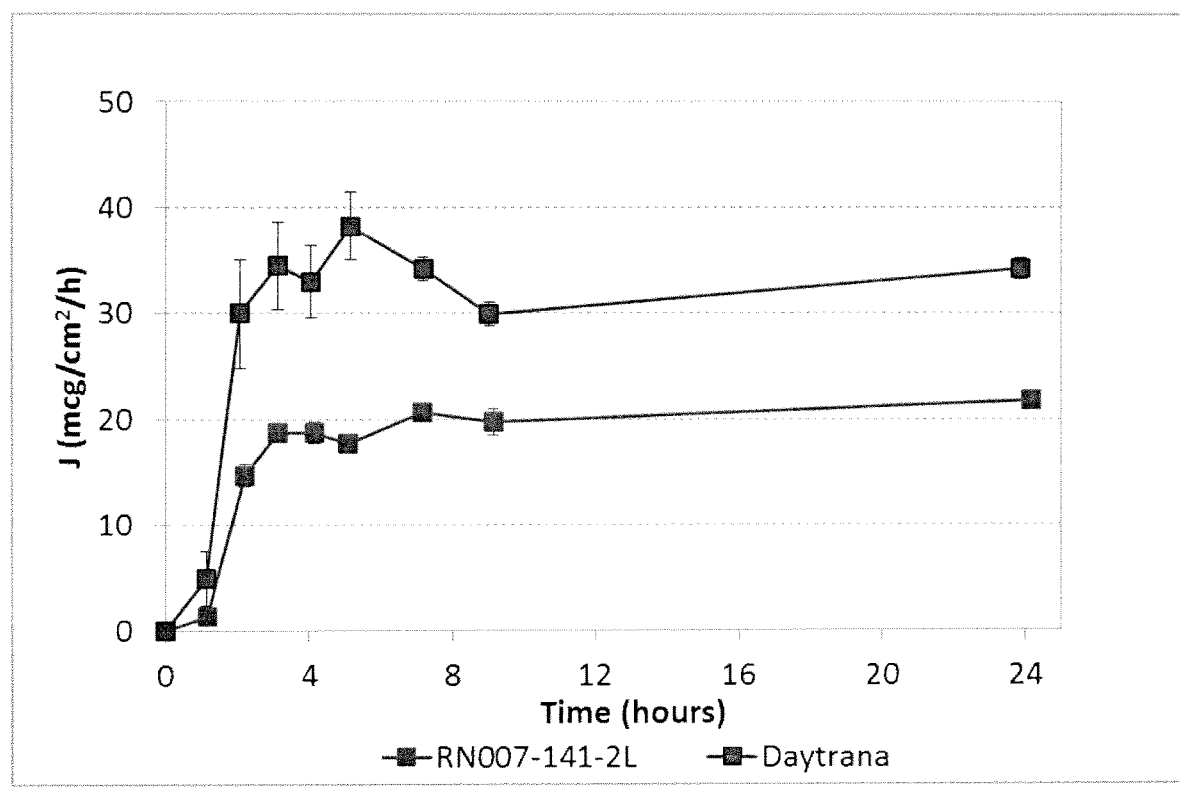
FIG. 2 shows in vitro flux data (flux, $\mu g/cm^2/hr$) of methylphenidate from a composition comprising an acrylic pressure-sensitive adhesive as compared to Daytrana®.

For comparison, the in vitro flux from a composition prepared with 20% methylphenidate in 80% acrylic pressure-sensitive adhesive (Gelva® 3087) and from Daytrana® are plotted in FIG. 2 and summarized below.

| Lot # | Formulation (SP 9732 Backing) | 94 hr Flux (mcg/cm²/h) | Flux Ratio |
|---|---|---|---|
| 40794 | Daytrana | 31.7 | 1.0 |
| RN007-141-2L | 20% MPH + 80% Gelva 3087 | 17.6 | 0.56 |

The results indicate that the acrylic pressure-sensitive adhesive achieves significantly lower flux than the polymer matrix of the Daytrana® product.

Example 3

The methylphenidate/polymer B composition described above was applied to a backing and a release liner, and peel force from the release liner was assessed over 4 months. Results as compared to results achieved with the commercial Daytrana® product are shown below.

| Lot # | Formulation (w/w) | Peel from Release Liner (g/0.5", n = 3) | | | |
|---|---|---|---|---|---|
| | | 1M | 2M | 3M | 4M |
| RN056-32-4L | Freshly made Daytrana | 9.2 | 22.4 | 39.9 | 80.6 |
| RN070-132-4L | 20% MPH + 80% Copolymer B | 23.3 | 25.0 | 22.4 | 18.7 |

The results show that the peel force for the polymer B composition remained stable and low while that of the Daytrana® product increased over time.

Example 4

Figure 3:
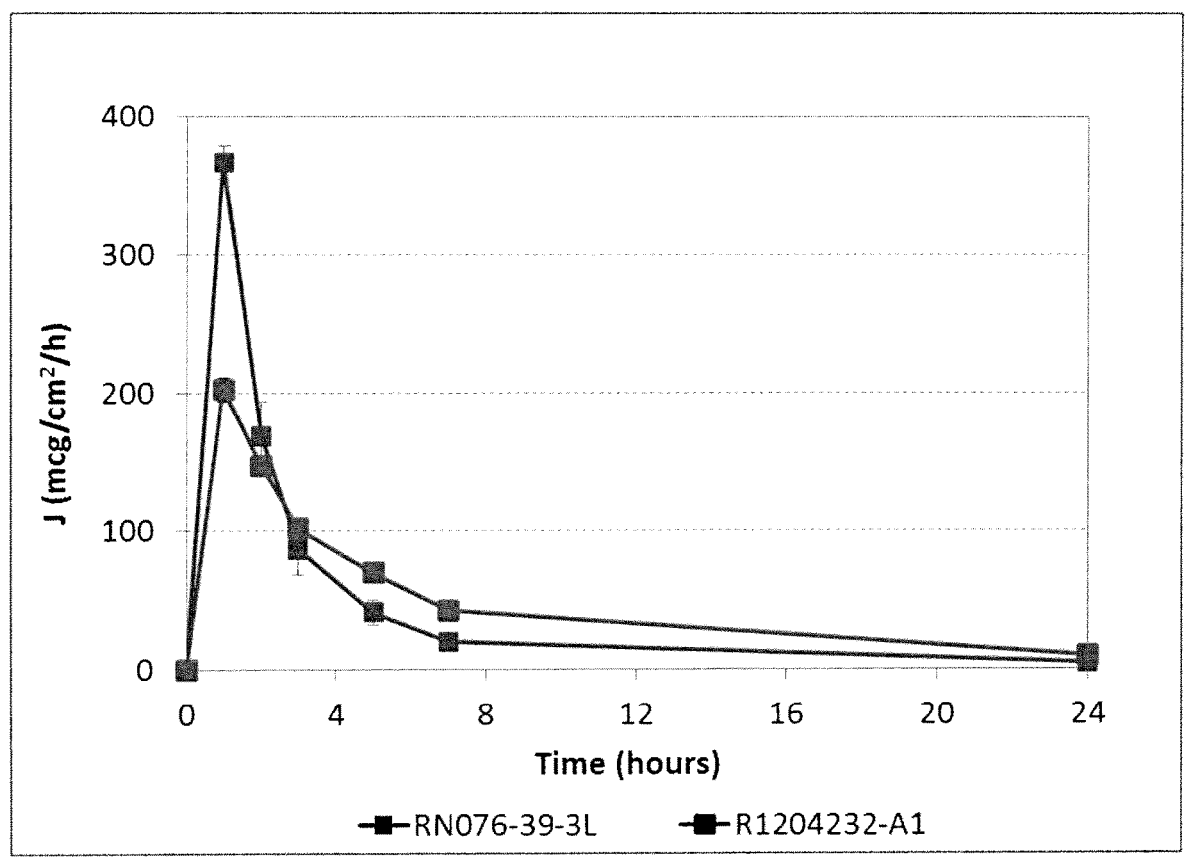
FIG. 3 shows in vitro flux data (flux, $\mu g/cm^2/hr$) of amphetamine from a composition comprising a silicone-containing acrylic polymer as described herein as compared to a composition comprising acrylic pressure-sensitive adhesives.

Amphetamine was formulated in silicone-containing acrylic polymer B (described above) to prepare a composition comprising 15% amphetamine and 85% polymer B. Drug flux through human cadaver skin over 24 hours was assessed in vitro. Results are shown in FIG. 3 as compared to flux from a polymer matrix composition prepared with 15% amphetamine in acrylic pressure-sensitive adhesive polymers with no silicone moiety.

The amphetamine/polymer B composition described above was applied to a backing and a release liner, and peel force from the release liner was assessed over 4 months. Results as compared to results achieved with the acrylic pressure-sensitive adhesive polymer matrix are shown below.

| Lot # | Formulation (w/w) | Peel from Release Liner (g/0.5", n = 3) | | | |
|---|---|---|---|---|---|
| | | 1M | 2M | 3M | 4M |
| RN049-64-4L | 15% Amphetamine + 42.5% Gelva 3087 + 42.5% BioPSA 4102 | 13.9 | 62.1 | 51.8 | 91.5 |
| RN076-39-3L | 15% Amphetamine + 85.0% copolymer B | — | 14.8 | 7.6 | 4.4 |

Example 5

Figure 4:
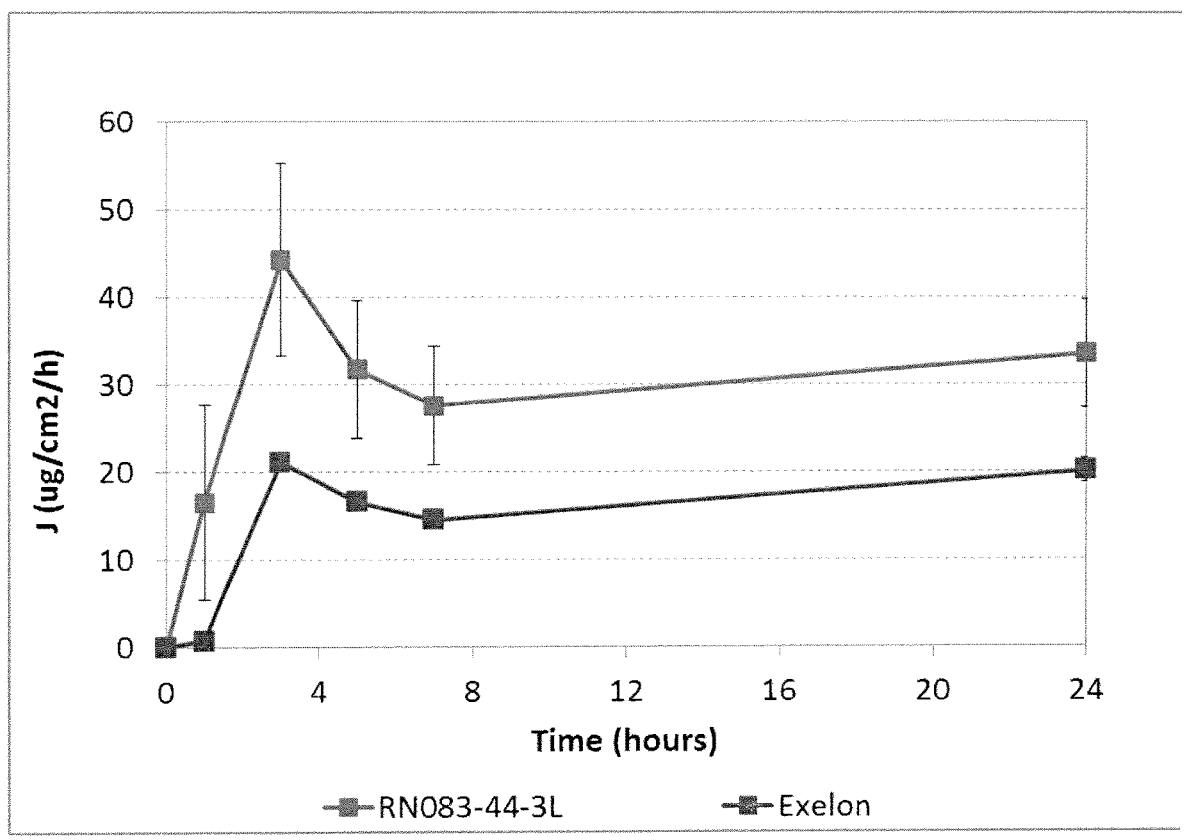
FIG. 4 shows in vitro flux data (flux, $\mu g/cm^2/hr$) of rivastigmine from a composition comprising a silicone-containing acrylic polymer as described herein as compared to Exelon®.

Rivastigmine was formulated in silicone-containing acrylic polymer B (described above) to prepare a composition comprising 20% rivastigmine and 80% polymer B. Drug flux through human cadaver skin over 24 hours was assessed in vitro. Results are shown in FIG. 4 as compared to flux from the commercial Exelon® product which includes 20% rivastigmine. The results show that the flux from the polymer B composition was significantly higher than that from the commercial Exelon® product.

| Lot # | Formulation (SP 9732 Backing) | 24 hr Flux (mcg/cm²/h) | Flux Ratio |
|---|---|---|---|
| Exelon | Exelon | 19.11 | 1.0 |
| RN083-44-3L | 20% Rivastigmine + 80% Copolymer B | 33.25 | 1.74 |

The rivastigmine/polymer B composition described above was applied to a backing and a release liner, and peel force from the release liner was assessed over 4 months.

| Lot # | Formulation (w/w) | Peel from Release Liner (g/0.5", n = 3) | | | |
|---|---|---|---|---|---|
| | | 1M | 2M | 3M | 4M |
| RN083-44-3L | 20% Rivastigmine + 80.0% copolymer B | 8.8 | 21.8 | 31.9 | 20.8 |

The results show that the peel force from release liner of the polymer B composition remained stable and low after storage for 4 months at ambient conditions.

Example 6

Figure 5:
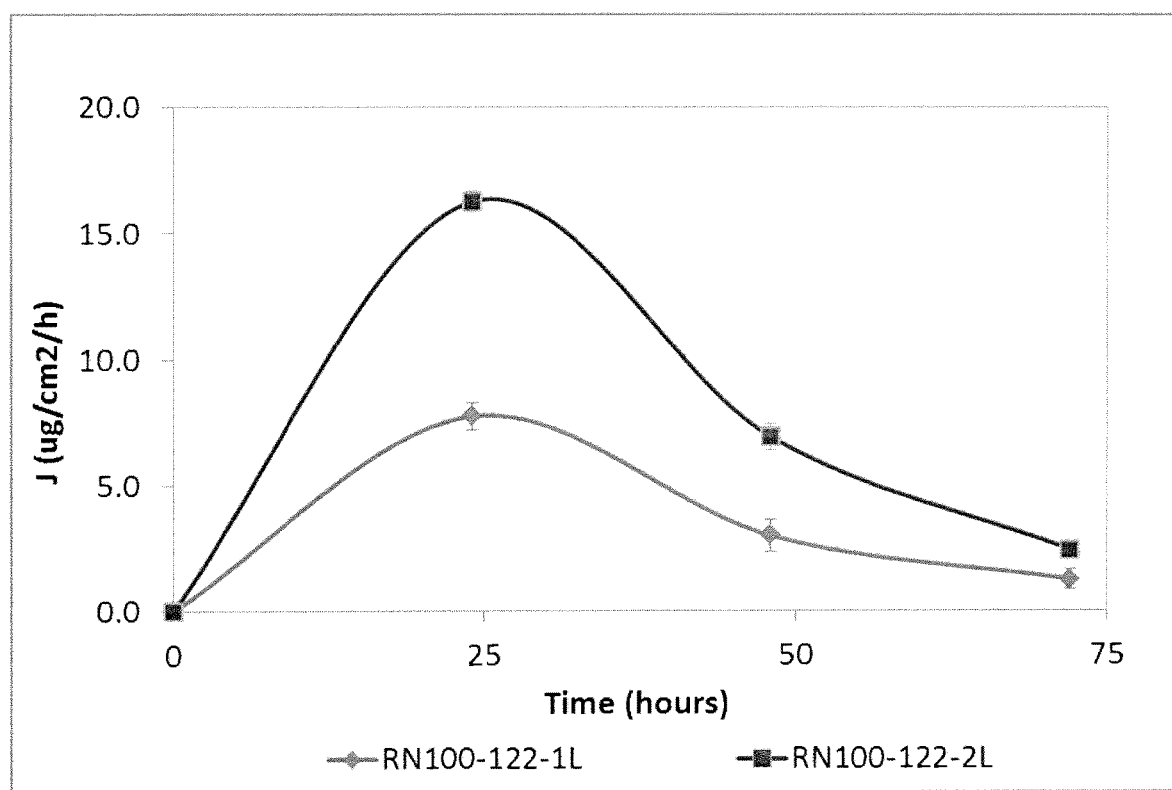
FIG. 5 shows in vitro flux data (flux, $\mu g/cm^2/hr$) of paroxetine from compositions comprising a silicone-containing acrylic polymer as described herein.

Paroxetine was formulated in silicone-containing acrylic polymer E (described above) to prepare compositions comprising 2.5% paroxetine and 97.5% polymer E and 5% paroxetine and 95% polymer E. Drug flux through human cadaver skin over 72 hours was assessed in vitro. Results are shown in FIG. 5. The results show that the flux from the polymer E composition was directly correlated with the drug-loading concentration.

The paroxetine/polymer E compositions described above were applied to a backing and a release liner, and peel force from the release liner was assessed over 4 months at ambient condition. Results are shown below.

| Lot # | Formulation (w/w) | Peel from Relase Liner (g/0.5", n = 3) | | |
|---|---|---|---|---|
| | | 0 | 2M | 4M |
| RN100-122-1L | 2.5% Paroxetine + 97.5% copolymer E | 37.5 | 29.3 | 21.7 |
| RN100-122-2L | 5% Paroxetine + 95% copolymer E | 42.4 | 19.2 | 17.0 |

The results show that the peel force from release liner of the polymer E composition remained low after storage for 4 months at ambient condition.

Example 7

Clonidine was formulated in silicone-containing acrylic polymer B, C, or D (described above) to prepare a composition comprising 2% clonidine and 98% polymer B, C or D. The compositions were applied to backings and release liners, and peel force from the release liner was assessed over 4 months at ambient condition.

| Lot # | Formulation (w/w) | Peel from Release Liner (g/0.5", n = 3) | | | |
|---|---|---|---|---|---|
| | | 1M | 2M | 3M | 4M |
| RN090-90-1L | 2% clonidine + 98.0% copolymer B | 10.4 | 14.6 | 12.4 | 13.6 |
| RN090-90-2L | 2% clonidine + 98.0% copolymer C | 10.8 | 14.3 | 14.4 | 16.6 |
| RN090-90-3L | 2% clonidine + 98.0% copolymer D | 10.9 | 14.3 | 17.1 | 22.5 |

The results show that the peel force from release liner of the silicone-containing acrylic polymer compositions remained low and stable after storage for 4 months at ambient condition.

What is claimed is:

1. A composition for the transdermal delivery of an amine drug through skin in the form of a flexible finite system for topical application to skin, comprising a polymer matrix comprising:
   an amine drug selected from amphetamine, methylphenidate, rivastigmine, paroxetine and clonidine, and
   a non-reactive silicone-containing acrylic polymer made from non-reactive methyl acrylate monomers, 2-ethylhexyl acrylate monomers, and mono-vinyl terminated polydimethylsiloxane that do not react with amine groups of the amine drug,
   wherein the non-reactive silicone-containing acrylic polymer constitutes at least 80% w/w of the dry weight of the polymer matrix, and
   wherein the composition exhibits a stable release liner peel force over 4 months, when assessed after application to a backing and release liner and storage over 4 months at ambient conditions.

2. The composition of claim 1, wherein the non-reactive silicone-containing acrylic polymer is the only polymer component of the polymer matrix.

3. The composition of claim 1, wherein the polymer matrix consists of the amine drug and non-reactive silicone-containing acrylic polymer, and, optionally, one or more components selected from antioxidants, skin permeation enhancers, tackifiers, plasticizers, and crosslinking agents.

4. The composition of claim 1, wherein the polymer matrix consists of the amine drug and non-reactive silicone-containing acrylic polymer.

5. The composition of claim 1, wherein the non-reactive silicone-containing acrylic polymer is comprised of 1-99% by weight acrylic monomers and 99-1% by weight silicone-containing acrylic monomers, based on the total dry weight of the polymer.

6. The composition of claim 1, wherein the non-reactive silicone-containing acrylic polymer is comprised of up to 50% by weight acrylic monomers and at least 50% by weight silicone-containing acrylic monomers, based on the total dry weight of the polymer.

7. The composition of claim 1, wherein the non-reactive silicone-containing acrylic polymer is comprised of at least 50% by weight acrylic monomers and up to 50% by weight silicone-containing acrylic monomers, based on the total dry weight of the polymer.

8. The composition of claim 1, further comprising a backing.

9. The composition according to claim 8, further comprising a release liner.

10. A composition for the transdermal delivery of an amine drug through skin in the form of a flexible finite system for topical application to skin, comprising a polymer matrix comprising:
    an amine drug selected from amphetamine and methylphenidate, and
    a non-reactive silicone-containing acrylic polymer made from non-reactive methyl acrylate monomers, 2-ethylhexyl acrylate monomers, and mono-vinyl terminated polydimethylsiloxane that do not react with amine groups of the amine drug,
    wherein the non-reactive silicone-containing acrylic polymer constitutes at least 80% w/w of the dry weight of the polymer matrix, and
    wherein the composition exhibits a stable release liner peel force over 4 months, when assessed after application to a backing and release liner and storage over 4 months at ambient conditions.

11. The composition of claim 10, wherein the amine drug is amphetamine.

12. The composition of claim 10, wherein the amine drug is methylphenidate.

13. A method for the transdermal delivery of an amine drug through skin of a subject in need thereof, comprising topically applying the composition of claim 1 to the skin of the subject.

\* \* \* \* \*